(12) United States Patent
Wu et al.

(10) Patent No.: US 8,766,028 B2
(45) Date of Patent: Jul. 1, 2014

(54) SEPARATING STYRENE FROM C6-C8 AROMATIC HYDROCARBONS

(75) Inventors: Kuang-Yeu Wu, Plano, TX (US); Adam T. Lee, Dallas, TX (US); Karl Tze-Tang Chuang, Edmonton (CA); Hung-Chung Shen, Chia-Yi (TW); Tzong-Bin Lin, Chia-Yi (TW)

(73) Assignees: AMT International Inc., Plano, TX (US); CPC Corporation, Taipei (TW)

( * ) Notice: Subject to any disclaimer, the term of this patent is extended or adjusted under 35 U.S.C. 154(b) by 194 days.

(21) Appl. No.: 13/373,094

(22) Filed: Nov. 4, 2011

(65) Prior Publication Data

US 2013/0116489 A1    May 9, 2013

(51) Int. Cl.
  *C07C 7/00* (2006.01)
  *C07C 7/148* (2006.01)
  *C07C 7/163* (2006.01)

(52) U.S. Cl.
  USPC ............ 585/804; 585/254; 585/809; 585/837

(58) Field of Classification Search
  USPC ....................................... 585/254
  See application file for complete search history.

(56) References Cited

U.S. PATENT DOCUMENTS 5,685,972 A * 11/1997 Timken et al. ............... 208/89
6,017,443 A * 1/2000 Buchanan .................... 208/210
6,262,314 B1 * 7/2001 Escalante et al. ............. 568/697
7,304,195 B2 * 12/2007 Choi et al. .................... 585/489
7,744,750 B2 * 6/2010 Brown et al. ................. 208/299
2009/0253942 A1 * 10/2009 Di Girolamo et al. ........ 568/697

FOREIGN PATENT DOCUMENTS

WO    WO 2008092232 A1 *    8/2008

OTHER PUBLICATIONS

Verevkin et al., Chemical equilibrium study in the reacting system of the (1-alkoxyethyl)benzene synthesis from alkanols and styrene, 2001, Journal of Chemical Engineering Data, vol. 46, pp. 984-990.*

* cited by examiner

*Primary Examiner* — In Suk Bullock
*Assistant Examiner* — Youngsul Jeong
(74) *Attorney, Agent, or Firm* — George A. Seaby

(57) ABSTRACT

The invention disclosed relates to a process for refining a hydrocarbon feed to make substantially styrene-free C6-C8 aromatic hydrocarbons (BTX). The hydrocarbon feed, for example, unhydrotreated pyrolysis gasoline, is distilled to make a BTX rich stream containing styrene which is fractionated to separate C6 and C7 hydrocarbons from C8 hydrocarbons including styrene. Styrene in the C8 hydrocarbons reacts in the presence of a selective etherification catalyst with a C1-C3 lower alkyl alcohol to form the corresponding styrene ether, which is then separated by distillation into a styrene ether stream and a C8 hydrocarbons rich stream. The C8 hydrocarbons rich stream is then re-mixed with the C6 and C7 hydrocarbons, and sent to hydrogenation reactors to remove sulphur and olefinic hydrocarbons to form substantially styrene-free BTX.

14 Claims, 10 Drawing Sheets

SEPARATING STYRENE FROM C6-C8 AROMATIC HYDROCARBONS

FIELD OF INVENTION

The present invention relates to a process for reducing the styrene content of a C6-C8 aromatic hydrocarbon blend, commonly known as BTX, in refining of hydrocarbons, by converting the styrene in the BTX mixture in the presence of a catalyst which is selective for etherification, by reaction with a C1-C3 lower-alkyl alcohol, such as methanol or ethanol, to form the corresponding styrene ether, which is subsequently separated from the BTX to form substantially styrene-free BTX. The resulting styrene ether may be decomposed to recover styrene. Alternatively, the styrene ether may be blended into gasoline as an oxygenate to improve combustion characteristics.

BACKGROUND OF THE INVENTION

Refining of liquid hydrocarbons and fractionation provides a series of streams of hydrocarbon products. A stream such as hydrocarbon feed, unhydrotreated pyrolysis gasoline from steam cracker, FCC naphtha or unhydrotreated coker naphtha is further refined to provide a mixture of C6-C8 aromatics, commonly referred to as BTX, comprising primarily benzene, toluene, ethyl benzene, styrene, sulphur compounds and a mixture of xylenes. For example, a process for production of BTX from FCC naphtha is described by Timken et al. in U.S. Pat. No. 5,685,972 issued in 1997.

BTX is a valuable feedstock for manufacture of petrochemicals and polymers, and is also used as fuel for internal combustion engines. However, its styrene content tends to polymerize and form higher molecular weight compounds that can interfere with processing of BTX as chemical feedstock, or can cause formation of gummy residue that interferes with feeding it for combustion. Hence the presence of styrene in BTX is undesirable when BTX is to be used as petrochemical feedstock or as a liquid fuel for internal combustion engines. The styrene content in BTX is reduced by conversion to ethyl benzene by hydrogenation. Timken et al. in U.S. Pat. No. 5,685,972 describe a "hydrofinishing" stage in conversion of FCC naphtha to both BTX and high octane gasoline.

However, ethylbenzene and styrene have low value when they are combusted as fuel. BTX from which styrene has been removed has higher value than BTX containing styrene. Further, styrene itself has much higher value when it is recovered for use in manufacture of polymers or petrochemicals when compared to its conversion to ethyl benzene for use as fuel. So far, none of the methods disclosed in, for example, U.S. Pat. Nos. 3,953,300, 4,031,153, and 5,849,982, are effective for removing and recovering styrene from BTX fractions such as pyrolysis gasoline and FCC gasoline, which contain a significant amount of sulphur compounds. This is because styrene is more reactive with hydrogen than thiophenic sulfur in hydrotreating which is the only way to desulfurize the purified styrene stream commercially.

What is required is a process that removes styrene from BTX fractions more efficiently than present BTX refining and separation processes, and converting that styrene to valuable polymers and petrochemical products.

SUMMARY OF THE INVENTION

According to one aspect of the present invention, a process is provided for reduction of the styrene content of a C6-C8 aromatic hydrocarbon (BTX) blend of a stream from refining of liquid hydrocarbons. A typical BTX containing feed from refineries contains about 33% styrene and 67% xylenes.

In one embodiment, a hydrocarbon feed stream containing BTX including styrene is fed to a catalytic converter where in the presence of a catalyst selective for etherification, the majority of the styrene content is reacted with a C1-C3 lower-alkyl alcohol, preferably methanol or ethanol, in the presence of an acidic catalyst selective for etherification to form the corresponding styrene ether. The resulting styrene ether is separated from the stream by distillation to form one fraction containing hydrocarbons including BTX with a greatly reduced styrene content but retaining most sulphur compounds, and another stream that contains the styrene ether. The hydrocarbons stream containing residual unreacted styrene is hydrogenated to form a product stream and separating substantially styrene-free C6-C8 aromatic hydrocarbons are separated from the product stream. The styrene ether then may be decomposed to recover styrene and the C1-C3 lower-alkyl alcohol. Alternatively, the styrene ether may be blended into gasoline as an oxygenate to improve combustion characteristics.

Note that although methanol or ethanol is preferred, C3 alcohols can also be used. However, they are more expensive.

In another embodiment of the invention, the selective etherification catalyst is a sulfonic acid based polymeric cation exchange resin. In another embodiment of the invention the acidic catalyst is a sulfonic acid, macroreticular polymeric resin based on cross-linked styrene divinylbenzene co-polymers, such as those sold by Rohm & Haas under the TMs Amberlyst 15WET, 35WET and 70. Such materials are well known to be selective for etherification reactions. For example Amberlyst 15WET is used in the production of MTBE and ETBE, so its reliability is well known. It is noted that the 15WET, 35WET and 70 designations are for variants useful at different reaction temperatures. For example, Amberlyst 15WET is ideal for an etherification reaction at up to 120° C., Amberlyst 35WET for up to 150° C. and Amberlyst 70 in the higher end of the temperature range. Details of the properties of these materials are available in the Rohm & Haas catalogue available on-line under AMBERLYST polymeric catalysts. Nafion® SAC-13 is another polymeric acidic sulfonic acid catalyst that can be used. However, its activity is lower than that of the Amberlyst series.

In yet another embodiment of the invention, the etherification reaction is effected in a temperature range of 80° C. to 150° C. In the temperature range of 80° C. to 120° C., Amberlyst 15WET is stable. We found 100° C. to be optimum because of the high selectivity to styrene ether.

In another embodiment of the invention, a molar excess of the alcohol is used. Preferably, when the alcohol is methanol (MeOH), the molar ratio of MeOH:styrene is 5:1.

It is also contemplated that inorganic acidic catalysts such as sulfated zeolite could be used to catalyze etherification but their activity is lower.

As will be apparent from the Detailed Description of the invention which follows, the composition of the product stream is dependent on the selection of the design of the reactor system in which the process is performed.

BRIEF DESCRIPTION OF THE DRAWINGS

For a more complete understanding of the present invention and for further objects and advantages thereof, reference is made to the following description taken in conjunction with the accompanying drawings.

DETAILED DESCRIPTION OF THE INVENTION

The following description comprises data obtained through laboratory experiments and simulations using ASPEN PLUS® software.

Figure 1:
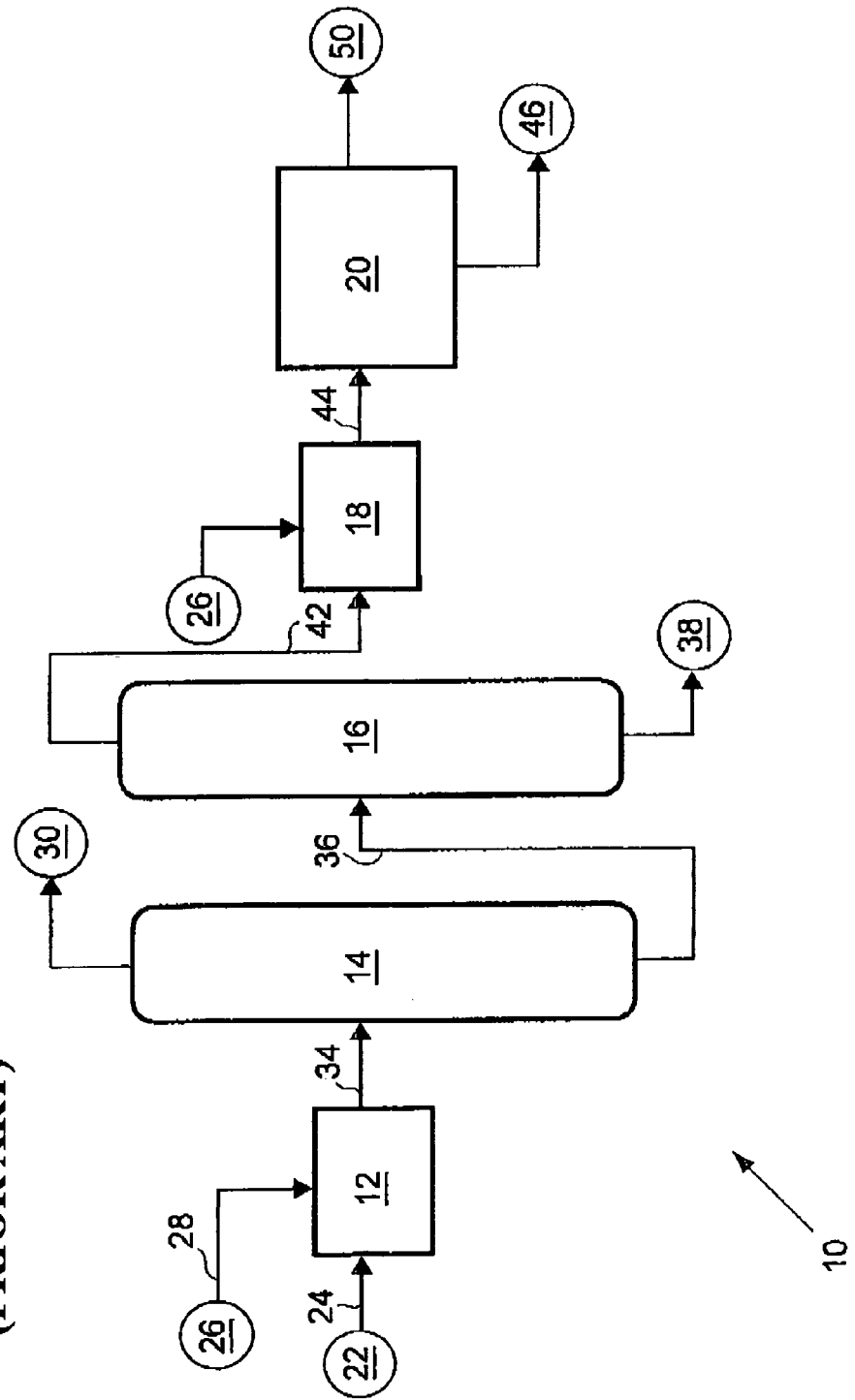
FIG. 1, labelled prior art, is a schematic flow diagram of a process for production of BTX.

FIG. 1, labelled PRIOR ART, illustrates schematically a typical process for production of BTX 50 having reduced styrene content from a hydrocarbon feed 22. Hydrocarbon feed 22 may be any refinery stream containing light aromatics, such as unhydrotreated pyrolysis gasoline, FCC naphtha or coker naphtha, having higher styrene content.

An apparatus 10 for the process has a sequence of reactors and columns including: a first stage hydrogenation reactor 12, a first distillation column 14, a second distillation column 16, a second stage hydrogenation reactor 18, and a liquid-liquid extraction section 20.

Hydrocarbon feed including styrene 22 is fed through a feed line 24 into first stage reactor 12 where it reacts with hydrogen 26 fed through a hydrogen feed line 28 over a first stage catalyst. The catalyst is conventional Pd or Ni supported on alumina so as to convert dienes in hydrocarbon feed 22 into mono-olefins. The product stream 34 from this reactor is fed into first distillation column 14 where it is separated into a light fraction 30 comprising mainly C5 hydrocarbons and a liquid bottoms fraction 36. Liquid bottoms fraction 36 is fed into second distillation column 16 where it is separated into a heavies fraction 38, comprising C9 and higher hydrocarbons, and a lighter fraction 42 comprising BTX, ethylbenzene and styrene. Lighter fraction 42 is fed into second stage hydrogenation reactor 18 where it reacts with hydrogen 26 over a second stage catalyst. The catalyst is a conventional two layer catalyst, including an upper layer of NiMo and lower layer of CoMo, to convert olefins into paraffins and to convert sulphur compounds into hydrogen sulfide. The hydrogen sulfide so formed is removed from the mixture downstream from second stage hydrogenation reactor 18. A product stream 44 from second stage hydrogenation reactor 18 is fed into liquid-liquid extraction section 20 where it is separated into a light raffinate 46 and a product 50 comprising BTX and a lesser amount of ethyl benzene. This is the process now being employed at most oil refineries. Styrene is hydrogenated (H2 consumption increases cost) into ethyl benzene (low value). The advantages of the present invention are listed later.

With reference to FIGS. 2 through 7B, three embodiments of the present invention will now be described, and the performance and advantages of the present invention over the prior art process illustrated in FIG. 1 will be shown.

Figure 2:
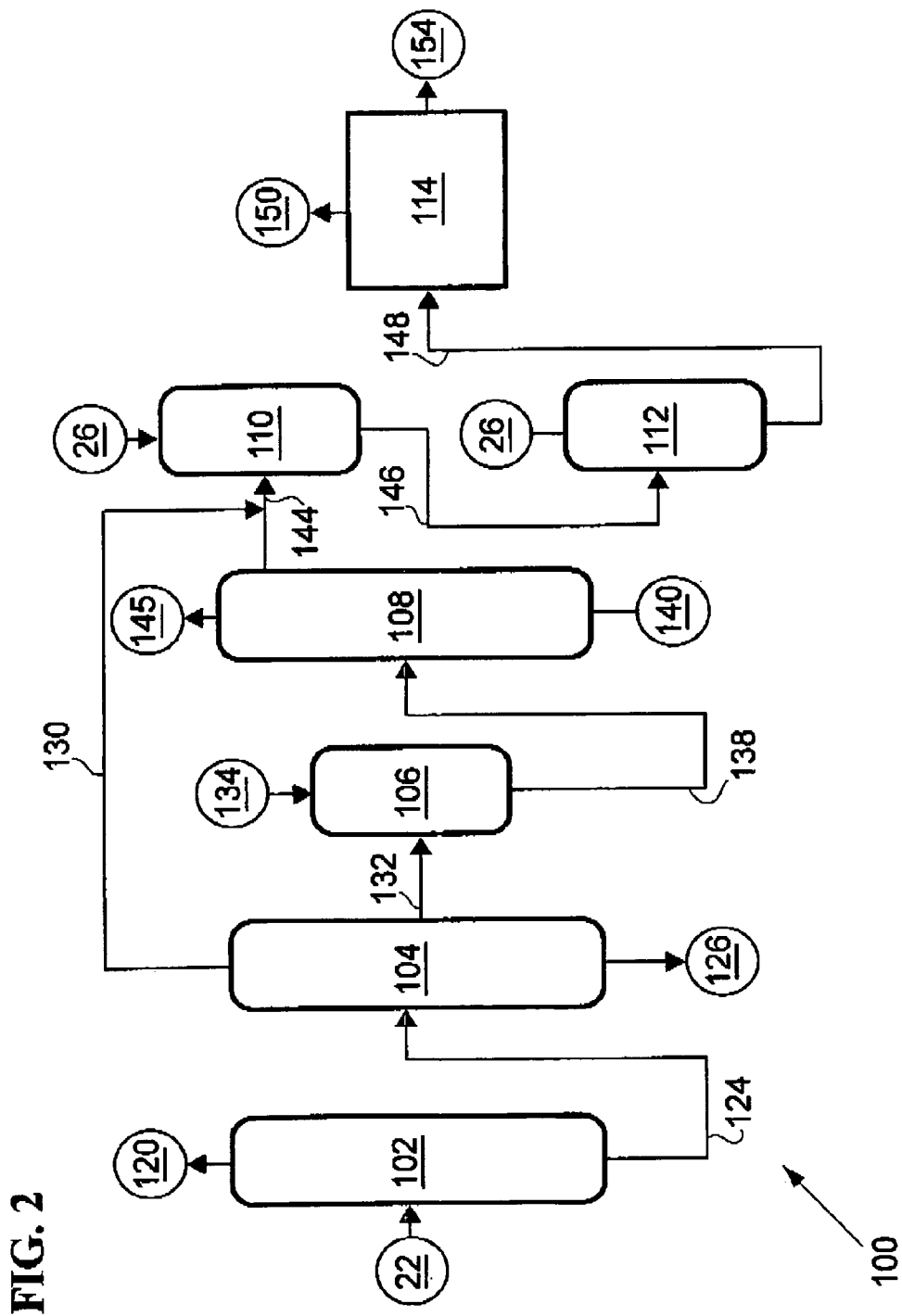
FIG. 2 is a schematic flow diagram of a first embodiment of a process for reduction of styrene content in BTX by conversion of styrene to a styrene ether.

FIG. 2 illustrates a first embodiment of the process of the present invention. An apparatus 100 for said process includes a first distillation column 102, a second distillation column 104, an etherification reactor 106, a third distillation column 108, a first stage hydrogenation reactor 110, a second stage hydrogenation reactor 112, and a BTX extraction section 114. Hydrocarbon feed containing styrene 22 is fed into first column 102 where it is separated by distillation into a distillate 120, comprising mainly C5 hydrocarbons, and a bottoms fraction 124 rich in C6-C8 aromatic hydrocarbons and containing styrene. Bottoms fraction 124 is fed into column 104 where it is distilled into a bottoms fraction 126, a middle fraction 132, and a distillate 130. Distillate 130 is rich in C6 and C7 aromatic hydrocarbons. Middle fraction 132 is rich in xylenes, styrene and ethyl benzene, that is C8 aromatic hydrocarbons. Bottoms fraction 126 comprises mainly C9+ hydrocarbons.

Middle fraction 132 a C1-C3 lower alkyl alcohol 134 are fed into etherification reactor 106, where they react over an acidic catalyst selective for etherification (not illustrated) to form an equilibrium mixture 138 rich in the corresponding styrene ether (Equation 1), wherein C1-C3 lower alkyl alcohol 134 is preferably methanol. Alternatively, ethanol may be used. It has been found experimentally that the selective etherification catalyst preferably is an acidic resin such as Amberlyst 15™ resin when reaction 1 is performed at about 100° C. Tests with a BTX feed containing about 33% styrene and 67% xylenes show very little difference in activity when using either Amberlyst 15WET or 35WET.

$$C_6H_5CH=CH_2 + CH_3OH \leftrightharpoons C_6H_5CH(CH_3)OCH_3 \qquad (1)$$

Figure 8:
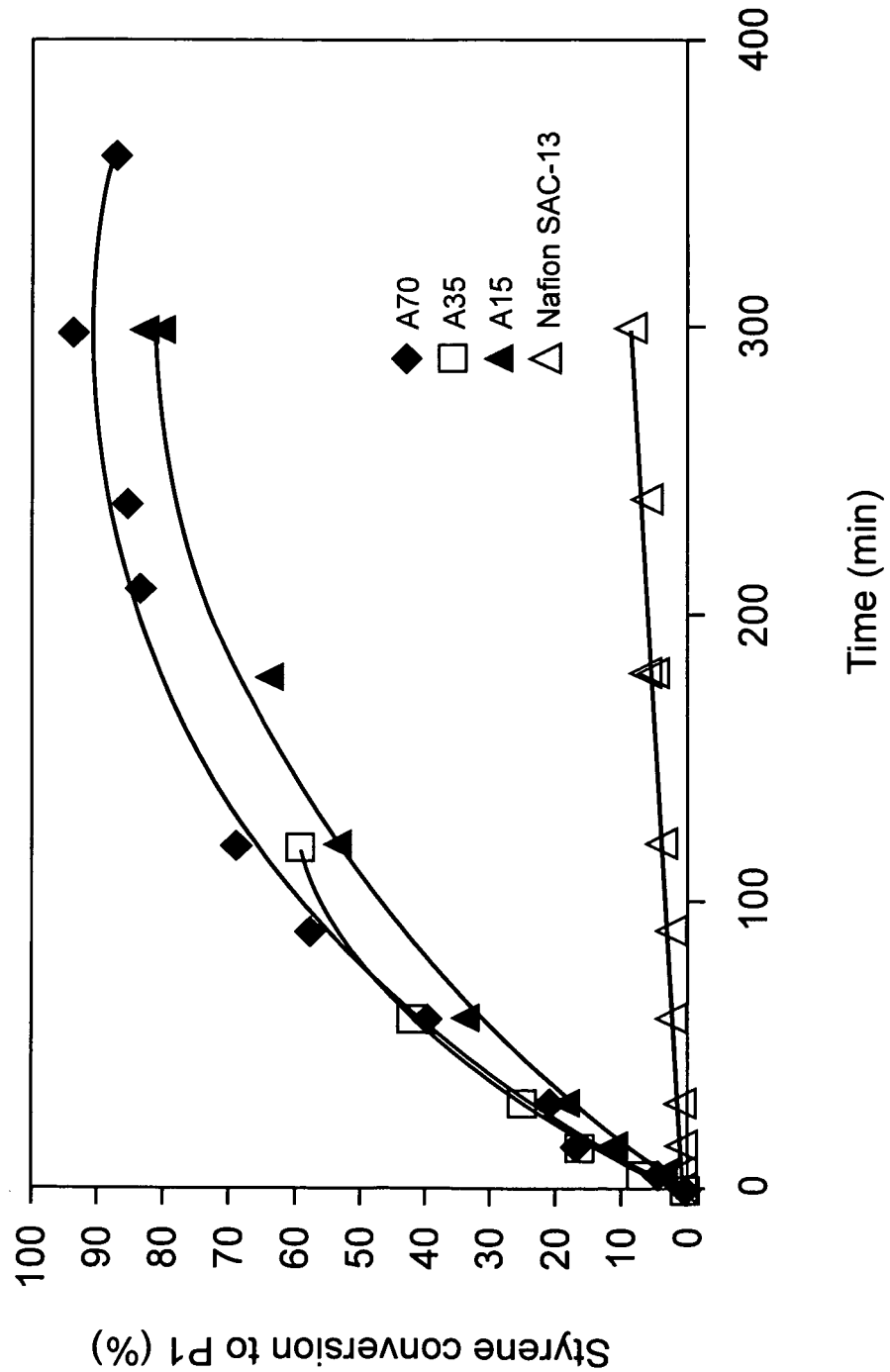
FIG. 8 is a graph illustrating the conversion of styrene to styrene ether, using various catalysts according to the invention.

As shown in FIG. 8, other similar acidic resin catalysts as described above can also be used. Specifically, FIG. 8, illustrates the conversion of styrene to styrene ether using 10 g of the various catalysts at a temperature of 100° C. at a molar feed ratio of MeOH:styrene of 5:1, at a stirrer speed of 1000 rpm.

Liquid equilibrium mixture 138 is fed into third distillation column 108 where it is fractionated into bottoms 140 rich in styrene ether, a distillate 144 rich in xylenes, containing residual unreacted styrene and substantially all the sulphur compounds, and a distillate 145 containing mainly unreacted methanol. Distillate 145 is recycled to the etherification reactor 106.

Distillate 130 from second distillation column 104 is co-fed with distillate 144 from third distillation column 108 and hydrogen 26 into first stage hydrogenation reactor 110 where they react over a first stage catalyst (same first stage catalyst as described above in [028]). A product stream 146 from first stage hydrogenation reactor 110 and hydrogen 26 are fed into a second stage hydrogenation reactor 112 where they react over a second stage catalyst (same second stage catalyst as described above in [028]) to saturate olefins and to desulfurize sulfur compounds. First stage hydrogenation reactor 110 and second stage hydrogenation reactor 112 operates under different conditions appropriate for the different reactions and catalysts used in each stage of the process, as will be familiar to those skilled in the art. For example, see the Axens' publication. A product stream 148 from second stage hydrogenation reactor 112 from which sulfur is removed is fed into BTX extraction section 114 where it is separated into a raffinate 150 and a product 154 rich in BTX and containing essentially no styrene or styrene ether.

When the C1-C3 lower-alkyl alcohol 134 was methanol and the ratio of methanol to styrene was 1:1 we obtained 78.2% conversion in the single etherification reactor 106 illustrated in FIG. 2. Optionally, in an adaptation of apparatus 100, product stream 138 from etherification reactor 106 may be fed into at least one additional etherification reactor arranged in series (not illustrated) where it reacts with additional methanol. The conversion using a sequence of two etherification reactors was 94%. Details of this adaptation are given in the Examples.

A concern was that methanol may be converted over the etherification catalyst to dimethyl ether (Equation 2). It was determined experimentally that there was no detectable product (by GC) from such a reaction, as shown by the products listed in the Tables in the Examples. The results indicate that the catalyst is more selective toward formation of styrene ether than toward formation of dimethyl ether.

$$2\ CH_3OH \leftrightarrows (CH_3)_2O + H_2O \quad (2)$$

Figure 3:
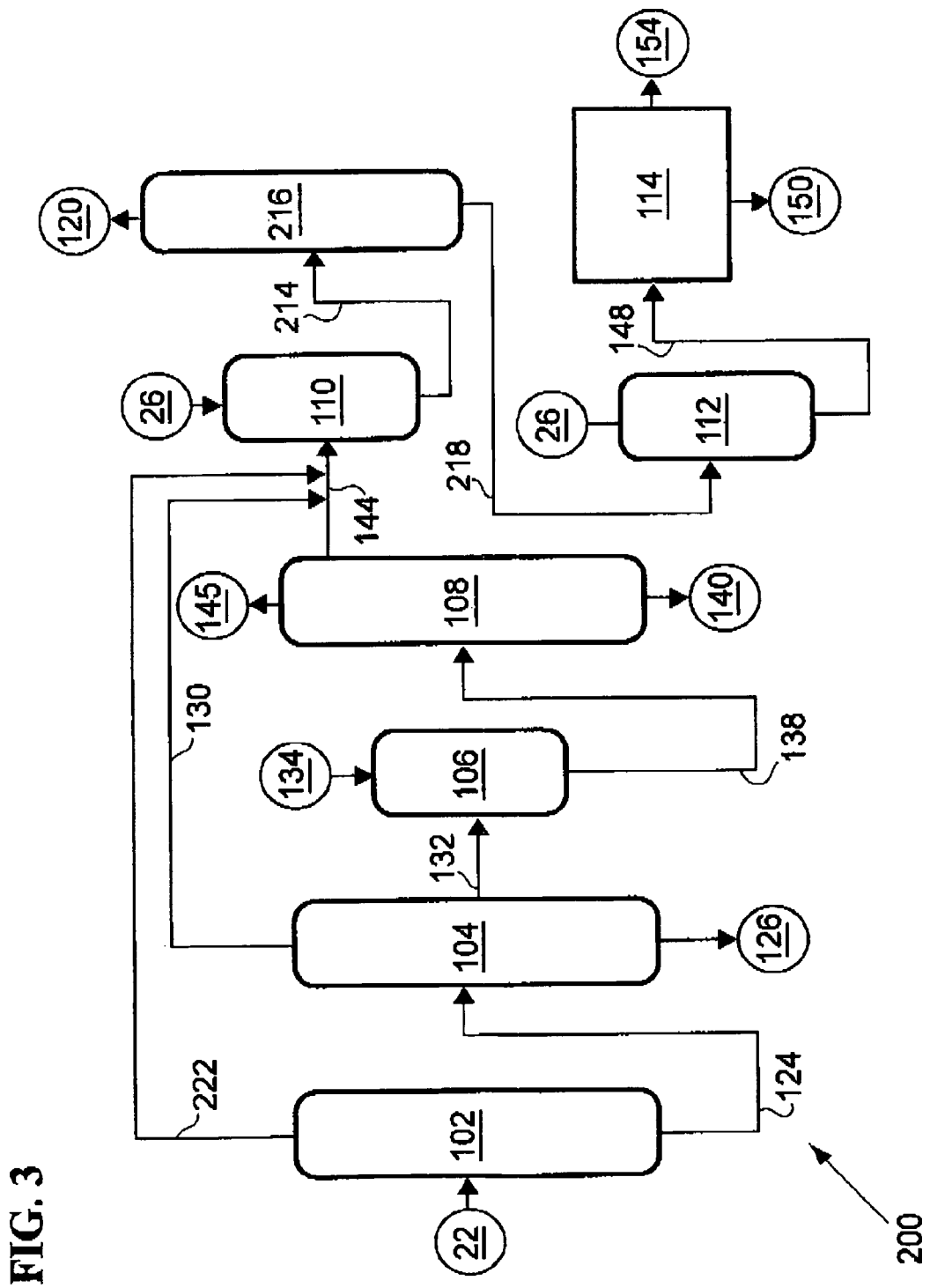
FIG. 3 is a schematic flow diagram of a second embodiment of a process for reduction of styrene content in BTX by conversion of styrene to a styrene ether.

FIG. 3 is a schematic illustration of a second embodiment of the process of the present invention. An apparatus 200 for the second embodiment of the process contains many elements found in apparatus 100 and these are identified using the same reference number. The differences in the second embodiment of the process are that distillate containing C5 hydrocarbons 222 from first distillation column 102 are co-fed with distillate containing C6 and C7 hydrocarbons 130 from second distillation column 104 and distillate 144 from third distillation column 108 into first stage hydrogenation reactor 110 where the olefins are hydrogenated by reaction with hydrogen 26 over the first stage catalyst (same first stage catalyst as in [028]). Also, a product stream 214 from first stage hydrogenation reactor 110 is fed into a fourth distillation column 216 where it is separated into a distillate 120 and a bottoms fraction 218. Distillate 120 comprises mainly C5 hydrocarbons. Bottoms fraction 218 is fed into second stage hydrogenation reactor 112 where olefins and sulfur compounds are hydrogenated to form a substantially sulphur-free product stream 148, as in the first embodiment of the process using apparatus 100.

It will be recognized that additional stages having further hydrogenation reactors and distillation columns may be incorporated to further refine the BTX product of the above embodiments.

Figure 4:
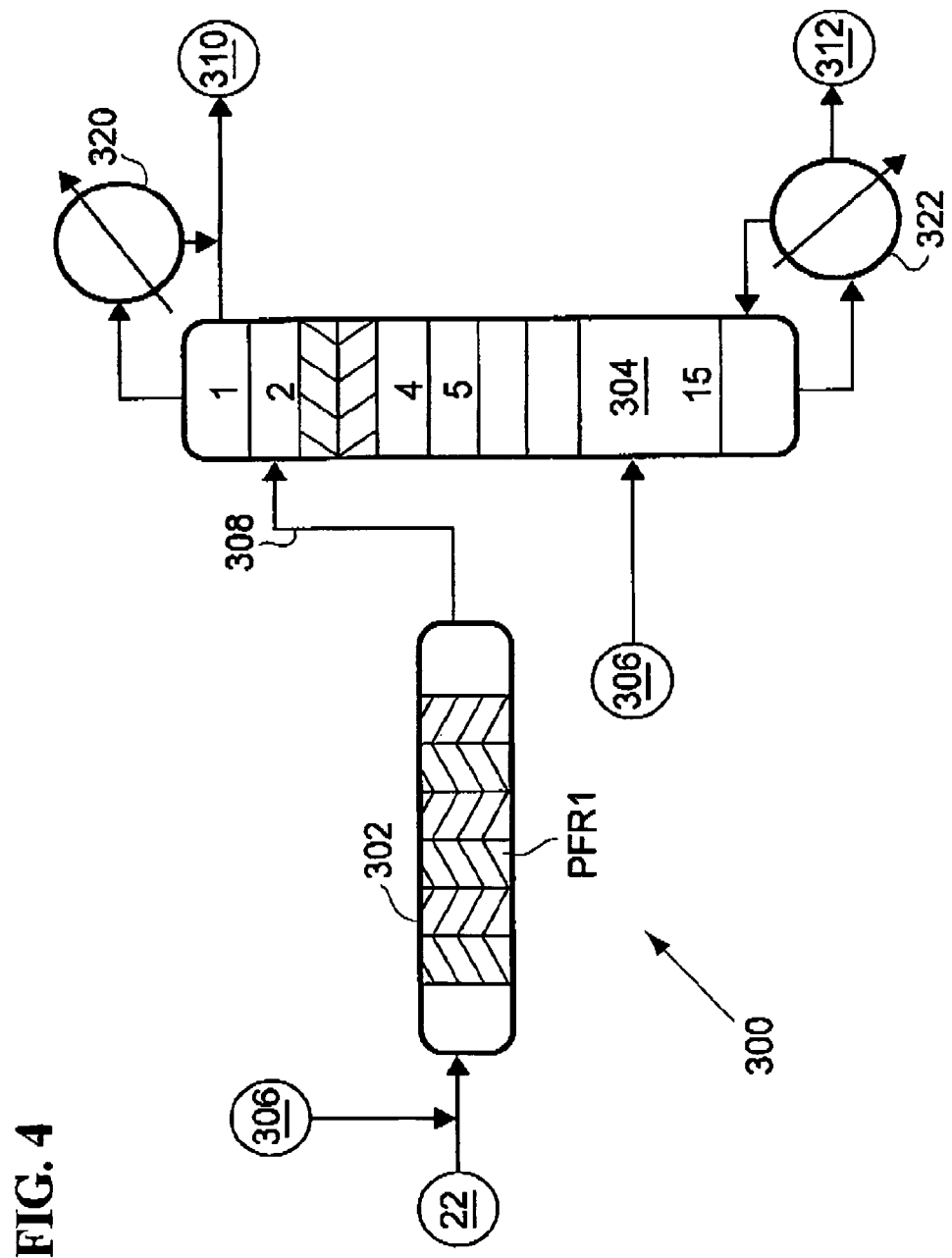
FIG. 4 is a schematic flow diagram of a third embodiment of a process for reduction of styrene content in BTX by conversion of styrene to a styrene ether in an apparatus having a pre-reactor and a catalytic distillation column.

FIG. 4 is a schematic illustration of a third embodiment of the process of the present invention. An apparatus 300 for third embodiment of the process includes a pre-reactor 302 and a catalytic distillation column 304. Hydrocarbon feed 22 first is reacted in pre-reactor 302 with a C1-C3 lower alkyl alcohol 306 selected from methanol and ethanol over a preferential acidic etherification catalyst as described above to form a stream 308 rich in the corresponding styrene ether, residual unreacted styrene, residual unreacted C1-C3 lower alkyl alcohol and C6-C8 aromatic hydrocarbons. Stream 308 and additional methanol or ethanol 306 are fed into catalytic distillation column 304 to react with residual unreacted styrene to recover a substantially styrene-free BTX product stream 310 and a liquid styrene ether stream 312. The catalytic distillation column 304, includes a condenser 320 at the top and a re-boiler 322 at the bottom. It is noted that this embodiment applies only to a hydrocarbon feed which is substantially pure BTX, since there are no provisions for removing lower and higher hydrocarbons from the feed. For this embodiment of the invention, the lower C5− and higher C9+ hydrocarbons are first separated by distillation and sent elsewhere at the refinery. This is described in FIG. 1. Accordingly, in this embodiment, we only deal with the cut of C6-C8 aromatics stream.

The processes modeled using ASPEN PLUS® have been characterized based on results from laboratory experiments, illustrated in the Examples below, and their advantages have been identified.

Advantages from operation of the process of the present invention when compared with prior art processes, especially for BTX aromatics from pyrolysis gasoline, are:

The BTX product contains little ethyl benzene derived from hydrogenation of styrene. In prior art processes the $C_8$ aromatics containing high amount of ethyl benzene typically is separated or sent to the gasoline pool, and so has low value. If the amount of ethyl benzene remaining in the $C_8$ aromatics is too high then the cost of downstream processing, for example purification of mixed xylenes, is increased.

Removal of the majority of the styrene before the stream is processed in the hydrogenation reactors reduces the volume that must be processed through those reactors, and so capacity of those reactors for processing the desired materials is increased. This is very significant since the hydrogenation reactors are normally the capacity bottlenecks in the naphtha cracker or gas oil cracker processes.

Further, the low amount of residual styrene enhances the operating lifetime of the catalysts in the hydrogenation reactors.

There is no need to consume hydrogen to convert styrene to ethyl benzene, and so hydrogen consumption is reduced for the overall process.

Styrene ether can either be blended into gasoline as an oxygenate to improve combustion characteristics or it may be decomposed back into styrene and methanol (reverse of Equation 1).

EXAMPLES

Example 1

Reaction of Methanol with Styrene in p-xylene in a Single Etherification Reactor A RPlug reactor model of Aspen Plus (Ver. 7.1) was used to model a plug flow reactor (PFR) for the reaction of styrene with methanol (Equation 1) to form methanol styrene ether (i.e. 1-methoxyethylbenzene, called MSE in Tables below). Laboratory rate data of the reaction in xylene solvent showed an empirical relationship that was directly proportional to styrene concentration and inversely proportional to methanol concentration. The model included consideration of the effect of methanol adsorption to account for an enhanced rate at low methanol concentrations, while also accounting for inhibition by methanol at high methanol concentrations. The reaction model also took into account the reverse reaction by including the equilibrium constant ($K_{eqm}$) which was taken from the literature (Verevkin et al., J. Chem. Eng. Data, 46, 984-990, 2001).

The NRTL-RK property method was used for vapor-liquid equilibrium calculations.

Binary interaction parameters were estimated for binary pairs involving MSE and for styrene-methanol.

Figure 5:
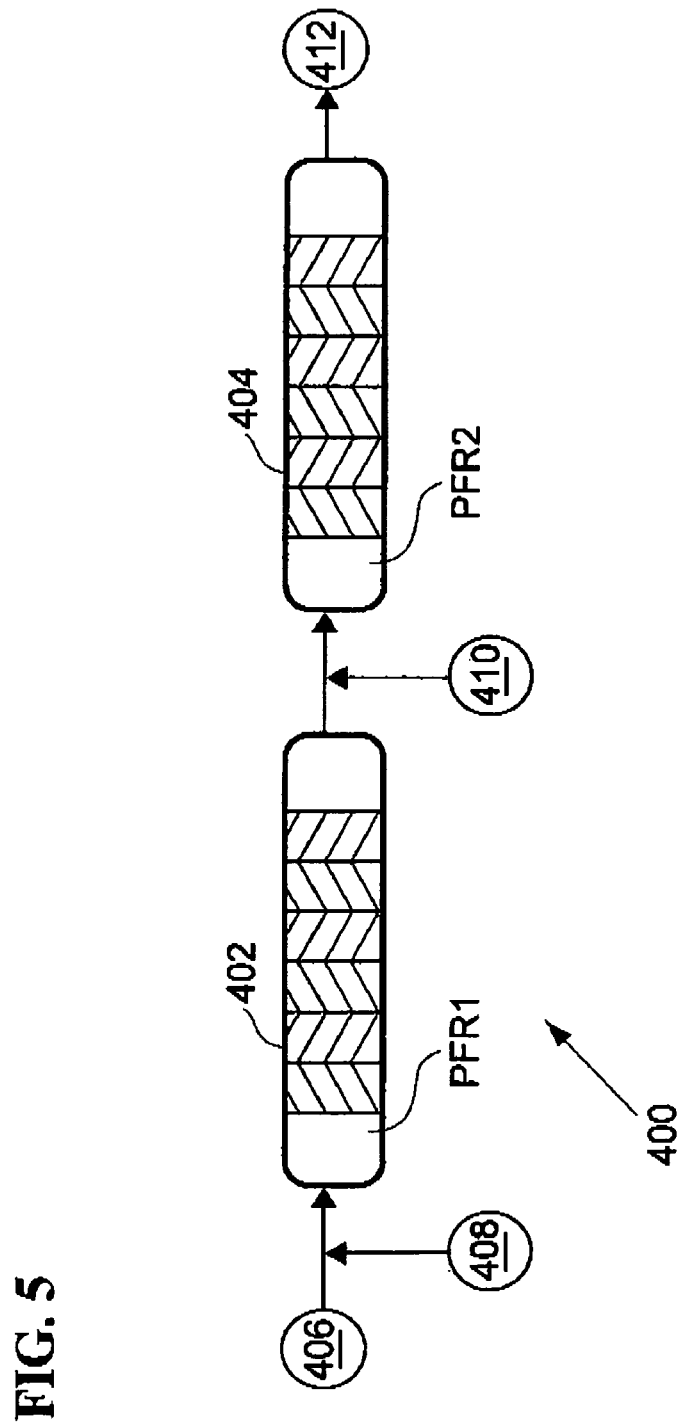
FIG. 5 is a schematic representation of the 2-stage plug flow reactor for modeling methanol styrene ether synthesis.
Figure 6A:
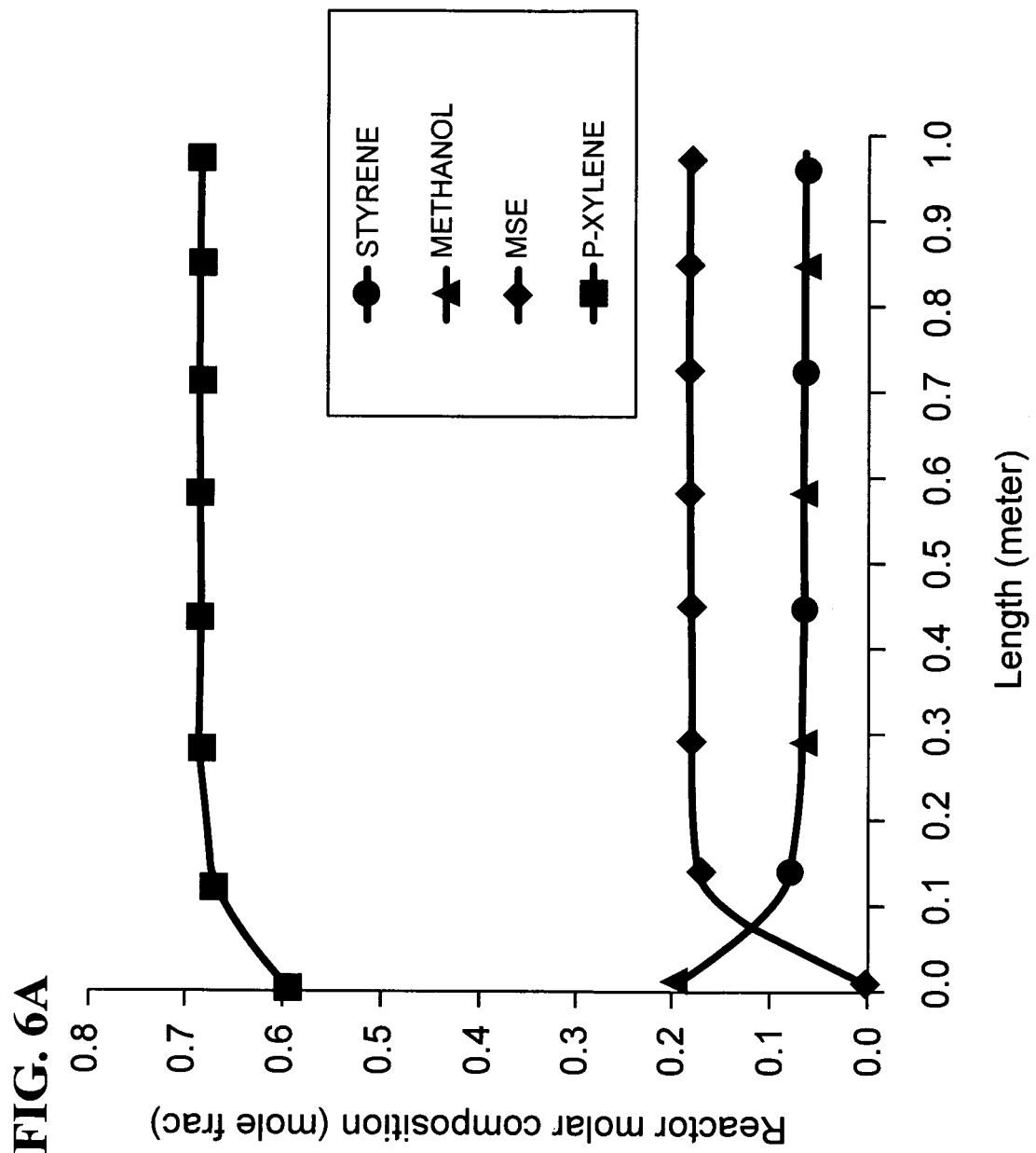
FIG. 6A is a graph showing a profile of composition of the reaction mixture as a function of distance along first reactor for reaction of methanol with styrene in p-xylene illustrated in FIG. 5.
Figure 6B:
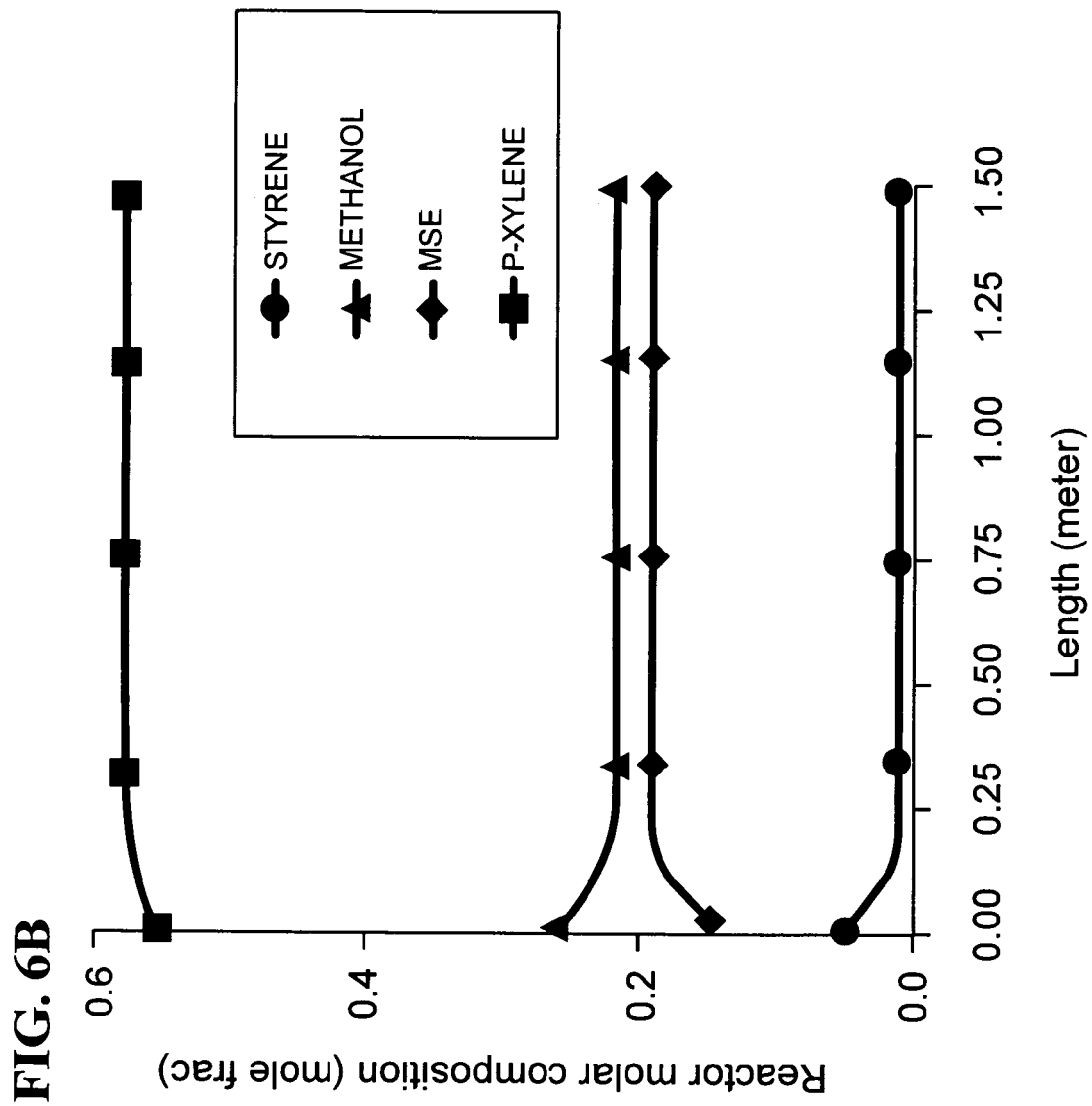
FIG. 6B is a graph showing a profile of composition of the reaction mixture as a function of distance along second reactor for reaction of additional methanol with styrene in p-xylene illustrated in FIG. 5.
Figure 7A:
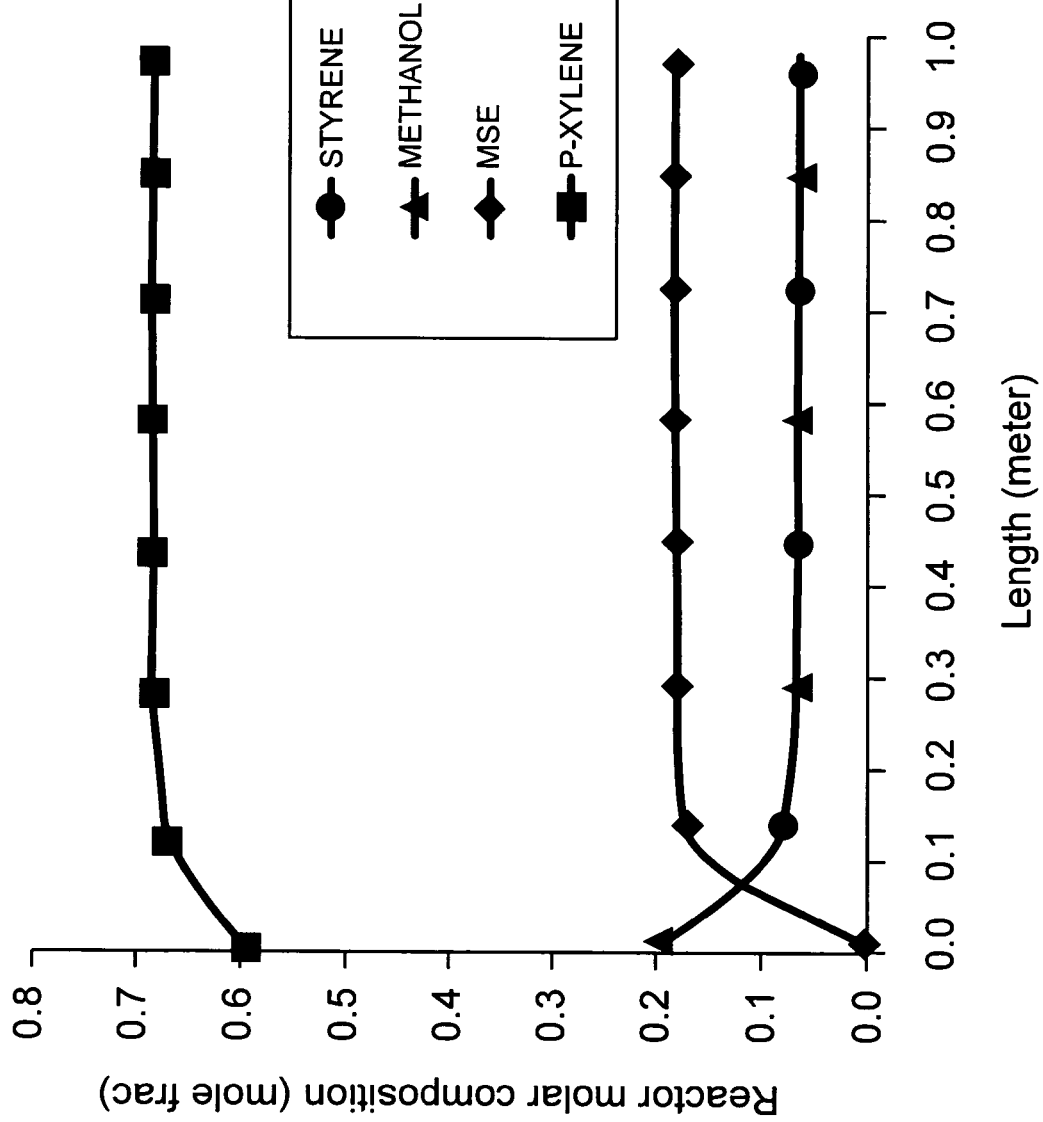
FIG. 7A is a graph showing a profile of composition as a function of distance along a pre-reactor for reaction of methanol with styrene in p-xylene to form a stream for feeding into a catalytic distillation column as illustrated in FIG. 4.
Figure 7B:
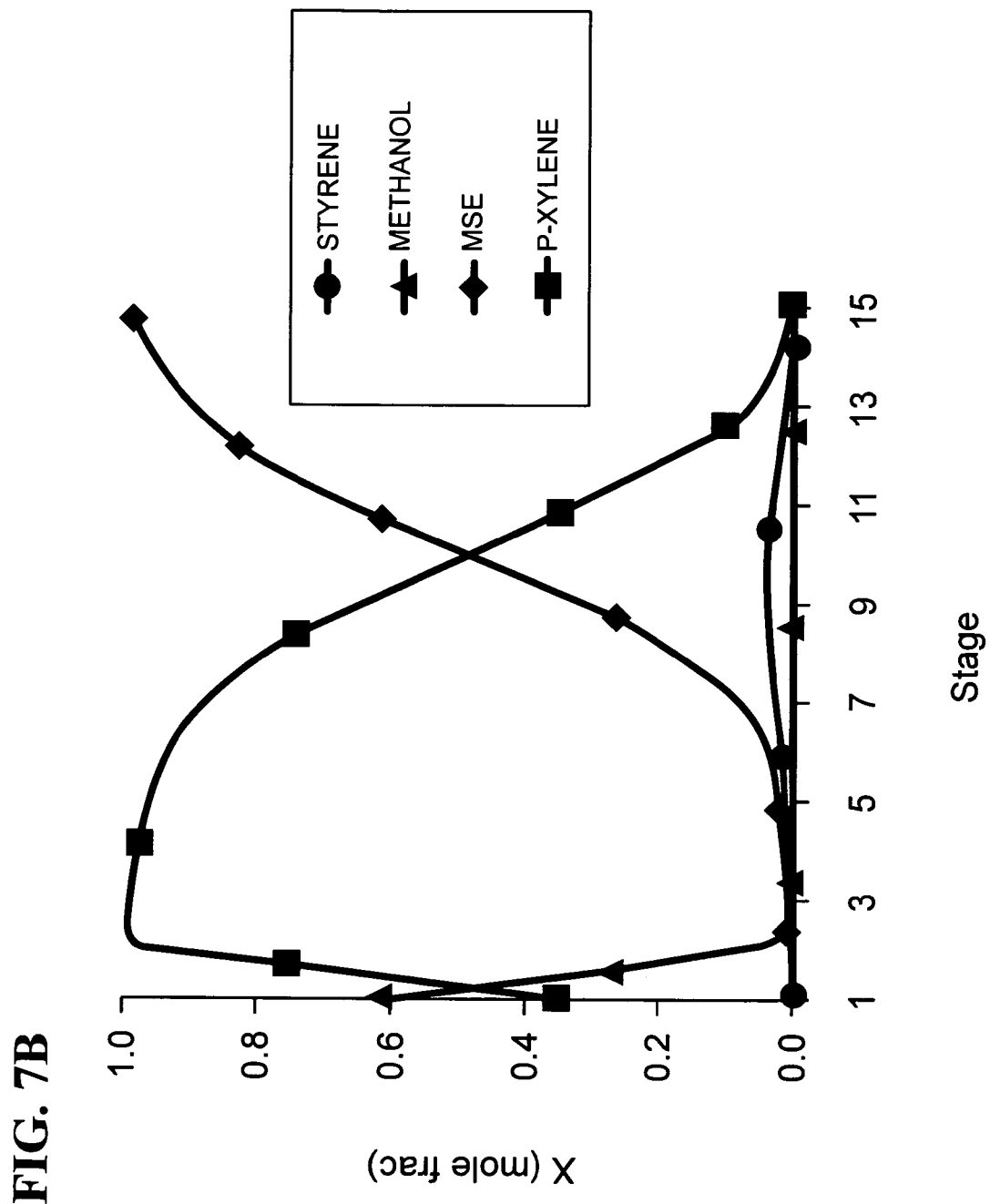
FIG. 7B is a graph showing a profile of composition as a function of height in the catalytic distillation column illustrated in FIG. 4.

The reactor was designed as a plug flow reactor, PFR. It was sized for a 1 mol/h flow of styrene in a feed mixture containing 0.35 mass fraction of styrene in xylene. FIG. 5 is a schematic representation of the 2-stage plug flow reactor apparatus 400 for methanol styrene ether synthesis. Table 1 shows the operating parameters of a first reactor 402 (labelled PFR1) and a second reactor 404 (labelled PFR2). The column is designed to operate at a pressure of 4 atm and a temperature of 100° C. A liquid feed 406 comprising styrene in xylene is mixed with the stoichiometric amount of methanol 408 equivalent to that of styrene before feeding into first reactor 402. The effluent 410 from first reactor 402 is mixed with an additional same amount of methanol 408 before feeding into second reactor 404. The effluent 412 from the second reactor 404 is mainly the corresponding styrene ether. Thus the overall feed ratio of methanol to styrene for the process was 2:1. FIG. 6 shows the liquid composition profile along the length of first reactor 402. It can be seen that equilibrium composition was obtained at 0.6 m from the reactor entrance. Table 2 is a stream summary for first reactor 402 (labelled PFR1) and second reactor 404 (labelled PFR2). Styrene conversion in first reactor 402 was 78.2% and the conversion in second reactor 404 of the residual styrene from first reactor 402 was 73.5%, for an overall styrene conversion of 94.2% to form the corresponding methanol-styrene ether 408. Thus with one reactor and methanol to styrene ratio of one, there was 78.2% conversion. By adding a second equivalent amount of methanol into the feed to the second reactor, the overall conversion for styrene was 94%.

Amerlyst 15WET is the catalyst used in the model calculations, in view of its stability, optimum activity and selectivity at the reaction temperature of 100° C. Other reaction temperatures may be used depending on the chosen catalyst.

TABLE 1

Operating parameters of the plug flow reactors

| Parameter | Value | |
| --- | --- | --- |
| | PFR1 | PFR2 |
| Reaction temperature (° C.) | 100 | 100 |
| Reactor pressure (atm) | 4 | 4 |
| Reactor length (m) | 1.5 | 1.5 |
| Reactor diameter (cm) | 2 | 2 |
| Catalyst loading (kg) | 0.8 | 0.8 |
| Bed voidage | 0.5 | 0.5 |

TABLE 2

Stream summary for PFR1 and PFR2

| | F1 | PFR1-OUT | F2 | PFR2-OUT |
| --- | --- | --- | --- | --- |
| Substream: MIXED Mole Flow mol/hr | | | | |
| STYRENE | 1 | 0.218 | 0.218 | 0.058 |
| METHANOL | 1 | 0.218 | 1.218 | 1.058 |
| MSE | 0 | 0.782 | 0.782 | 0.942 |
| P-XYLENE | 2.860 | 2.860 | 2.860 | 2.860 |
| WATER | 0 | 0 | 0 | 0 |
| DME | 0 | 0 | 0 | 0 |
| Mole Fraction | | | | |
| STYRENE | 0.206 | 0.054 | 0.043 | 0.012 |
| METHANOL | 0.206 | 0.054 | 0.240 | 0.215 |
| MSE | 0 | 0.192 | 0.154 | 0.192 |
| P-XYLENE | 0.588 | 0.701 | 0.563 | 0.582 |
| WATER | 0 | 0 | 0 | 0 |
| DME | 0 | 0 | 0 | 0 |
| Total Flow mol/hr | 4.860 | 4.078 | 5.078 | 4.918 |

Example 2

Reaction of Ethanol with Styrene in p-xylene in a Sequence of Two Reactors

In a similar set of measurements and modeling we showed that the rates of reactions with ethanol and methanol are similar, and similar slates of products are formed in similar proportions with either alcohol.

Example 3

Reaction of Methanol with Styrene in p-xylene in a Sequence of a Pre-Reactor and a Catalytic Distillation Column Referring to FIG. 4, an alternate configuration of an apparatus 300 provides for a third embodiment of the process described above. The process involves a pre-reactor (PFR1) 302 upstream of a catalytic distillation (CD) column 304. Pre-reactor 302 is a plug flow reactor with the same operating conditions as PFR1 in Table 1, for first reactor 402 described in Example 1 and illustrated in FIG. 5, and catalytic distillation column 304 is downstream of pre-reactor 302. Catalytic distillation column 304 operates with a total condenser 320 and a reboiler 322. CD column 304 as modeled has 15 stages and is operated at a pressure of 1 atm. The reaction zone temperature is between 104° C. and 133° C. Hydrocarbon feed 22 and a stoichiometric amount of methanol 306 equivalent to the styrene content of hydrocarbon feed 22 are mixed and fed to pre-reactor 302. The effluent from pre-reactor 302 is fed above stage 2 of CD column 304. Additional methanol 306 is fed below stage 3, so as to react with residual styrene in the effluent from pre-reactor 302 and thereby achieve high overall conversion of styrene (99%). Table 3 gives the operating parameters of pre-reactor 302 and catalytic distillation column 304. The overall feed ratio of methanol:styrene for the process as modeled is 6:1. Table 4 is a stream summary for pre-reactor 302 and for catalytic distillation column 304, and Table 5 shows stage profiles for catalytic distillation column 304.

TABLE 3

Operating parameters of the PRE-REAC and CD column

| Parameter | Value | |
| --- | --- | --- |
| | PRE-REAC | CD |
| Reaction temperature (° C.) | 100 | 104 to 133 |
| Reactor pressure (atm) | 4 | 1 |
| Reactor length (m) | 1.5 | — |
| Reactor diameter (cm) | 2 | — |
| Catalyst loading (kg) | 0.8 | 1.0/stage |
| Bed voidage | 0.5 | — |
| D/F ratio | — | 0.865 |
| Reflux ratio | — | 5 |
| Reaction stages | — | 2-3 |

TABLE 4

Stream summary for PRE-REAC and CD

|  | PR-OUT | M1 | B1 | D1 |
|---|---|---|---|---|
| Substream: MIXED Mole Flow mol/hr | | | | |
| STYRENE | 0.218 | 0 | 0.003 | 0.003 |
| METHANOL | 0.218 | 5 | 0.000 | 5.006 |
| MSE | 0.782 | 0 | 0.990 | 0.004 |
| P-XYLENE | 2.860 | 0 | 0.020 | 2.840 |
| WATER | 0 | 0 | 0 | 0 |
| Mole Frac | | | | |
| STYRENE | 0.054 | 0 | 0.003 | 0.000 |
| METHANOL | 0.054 | 1 | 0.000 | 0.638 |
| MSE | 0.192 | 0 | 0.977 | 0.000 |
| P-XYLENE | 0.701 | 0 | 0.020 | 0.362 |
| WATER | 0 | 0 | 0 | 0 |
| Total Flow mol/hr | 4.078 | 5 | 1.014 | 7.853 |
| Temperature C. | 100 | 25 | 171.53 | 66.71 |
| Pressure atm | 5 | 3 | 1 | 1 |
| Vapor Frac | 0 | 0 | 0 | 0 |
| Liquid Frac | 1 | 1 | 1 | 1 |
| Solid Frac | 0 | 0 | 0 | 0 |
| Enthalpy kJ/kmol | −40386.1 | −238597 | −123508 | −154328 |

1. wherein the etherification catalyst is an acidic cation exchange resin catalyst.

TABLE 5

Stage profiles for CD Column

| Stage | Temp (°C.) | Heat Duty (Watt) | Liquid (mol/hr) | Vapor (mol/hr) | Liquid Mole Fraction | | | |
|---|---|---|---|---|---|---|---|---|
| | | | | | STYRENE | METHANOL | MSE | P-XYLENE |
| 1 | 66.71 | 511.2 | 39.26 | 0.00 | 0.0004 | 0.6375 | 0.0005 | 0.3616 |
| 2 | 104.27 | " | 36.01 | 47.12 | 0.0013 | 0.0273 | 0.0037 | 0.9677 |
| 3 | 133.18 | " | 41.12 | 43.84 | 0.0008 | 0.0033 | 0.0109 | 0.9850 |
| 4 | 134.42 | " | 41.33 | 49.18 | 0.0064 | 0.0026 | 0.0139 | 0.9771 |
| 5 | 134.66 | " | 41.22 | 49.39 | 0.0124 | 0.0025 | 0.0211 | 0.9640 |
| 6 | 135.07 | " | 45.89 | 49.28 | 0.0185 | 0.0025 | 0.0376 | 0.9413 |
| 7 | 140.03 | " | 46.38 | 48.96 | 0.0241 | 0.0001 | 0.0748 | 0.9010 |
| 8 | 142.04 | " | 45.32 | 49.44 | 0.0285 | 0.0001 | 0.1500 | 0.8215 |
| 9 | 145.56 | " | 43.77 | 48.38 | 0.0303 | 0.0001 | 0.2797 | 0.6899 |
| 10 | 150.86 | " | 46.91 | 46.77 | 0.0286 | 0.0001 | 0.4550 | 0.5164 |
| 11 | 157.71 | " | 45.61 | 45.89 | 0.0218 | 0.0000 | 0.6503 | 0.3279 |
| 12 | 163.76 | " | 44.99 | 44.60 | 0.0147 | 0.0000 | 0.8041 | 0.1812 |
| 13 | 167.92 | " | 44.81 | 43.98 | 0.0090 | 0.0000 | 0.8997 | 0.0912 |
| 14 | 170.30 | " | 44.77 | 43.79 | 0.0053 | 0.0000 | 0.9512 | 0.0435 |
| 15 | 171.53 | 516.93 | 1.01 | 43.76 | 0.0030 | 0.0000 | 0.9769 | 0.0201 |

The invention claimed is:

1. A process for manufacture of substantially styrene-free C6-C8 aromatic hydrocarbons comprising:
   (a) providing a hydrocarbon feed containing C6-C8 aromatic hydrocarbons and styrene;
   (b) reacting majority of the styrene in the hydrocarbon feed with a C1-C3 alkyl alcohol in the presence of an acidic catalyst selective for etherification to produce an effluent comprising corresponding styrene ether;
   (c) separating the effluent by distillation to recover a liquid stream rich in the styrene ether and a volatiles stream rich in C6-C8 aromatic hydrocarbons, residual unreacted styrene and sulphur compounds;
   (d) hydrogenating the volatiles stream to form a product stream; and
   (e) separating substantially styrene-free C6-C8 aromatic hydrocarbons from the product stream.

2. The process of claim 1 comprising before step (b):
   (i) distilling the hydrocarbon feed to obtain a stream rich in C6-C8 aromatic hydrocarbons and a stream comprising C5 hydrocarbons;
   (ii) distilling said stream rich in C6-C8 aromatic hydrocarbons to obtain a first stream rich in C6 and C7 aromatic hydrocarbons, a second stream containing C9 and higher hydrocarbons and a third stream rich in xylenes, ethyl benzene and styrene; and
   (iii) passing the third stream to step (b).

3. The process of claim 2, wherein, in step (d), the volatiles stream is combined with the first stream rich in C6 and C7 hydrocarbons, and the combined streams are hydrogenated in successive reactors for the hydrogenation of olefins, sulphur compounds and residual unconverted styrene to form a hydrocarbon product stream, and in step (e) the substantially styrene-free C6-C8 aromatic hydrocarbons are separated from the hydrocarbon product stream by liquid-liquid extraction.

4. The process claim 3, including repeating step (b) before step (c) to form additional styrene ethers.

5. The process of claim 4, wherein the etherification is conducted in a series of sequential reactors comprising mixing the C1-C3 alkyl alcohol selected from methanol and ethanol with an effluent from drownstream of each reactor before introducing the mixture to an upstream reactor, wherein there is an overall excess of said C1-C3 alkyl alcohol to styrene in the hydrocarbon feed.

6. The process of claim 1, wherein a molar excess of the C1-C3 alkyl alcohol to styrene is used in step (b).

7. The process of claim 6, wherein the C1-C3 alkyl alcohol is methanol or ethanol.

8. The process of claim 7, wherein the etherification reaction is performed at a temperature of 80 to 150° C.

9. The process of claim 8, wherein the etherification reaction is performed at a temperature of about 100° C.

10. The process of claim 9, wherein the alcohol is methanol and the molar ratio of methanol:styrene is 5:1.

11. The process of claim 7, wherein the acidic catalyst is an acidic cation exchange resin catalyst.

12. The process of claim 1 comprising:
   (f) decomposing the styrene ether in the liquid stream to recover styrene and alcohol.

13. The process of claim 1, wherein the styrene ether is recovered for blending with gasoline to improve combustion characteristics.

14. The process of claim 2, wherein step (d) comprises:
   (i) combining the volatiles stream with the first stream rich in C6 and C7 hydrocarbons and the stream comprising C5 hydrocarbons to form a mixture;

(ii) passing the mixture to a first hydrogenation reactor to produce an effluent;
(iii) passing the effluent to a distillation column to obtain an overhead stream comprising C5 hydrocarbons and a bottom stream; and
(iv) passing the bottom stream to a second hydrogenation reactor to hydrogenate olefins and sulphur compounds contained therein, wherein the two hydrogenation reactors are in succession with the distillation column located between said two reactors.

* * * * *